(12) United States Patent
Schaller et al.

(10) Patent No.: US 8,167,898 B1
(45) Date of Patent: May 1, 2012

(54) FLEXIBLE CUTTER FOR SURGICAL STAPLER

(75) Inventors: Michael P. Schaller, Palo Alto, CA (US); Michael Murillo, Palo Alto, CA (US); Nathan H. White, Redwood City, CA (US); Hung K. Nguyen, San Jose, CA (US)

(73) Assignee: Cardica, Inc., Redwood City, CA (US)

( * ) Notice: Subject to any disclaimer, the term of this patent is extended or adjusted under 35 U.S.C. 154(b) by 235 days.

(21) Appl. No.: 12/435,653

(22) Filed: May 5, 2009

(51) Int. Cl.
*A61B 17/32* (2006.01)

(52) U.S. Cl. ........................ 606/167; 227/180.1; 606/159

(58) Field of Classification Search .................. 606/153, 606/167, 219, 220, 155, 156, 170, 171, 172, 606/154; 227/180.1, 178.1; 30/278, 335
See application file for complete search history.

(56) References Cited

U.S. PATENT DOCUMENTS

| | | | |
|---|---|---|---|
| 3,254,650 | A | 6/1966 | Collito |
| 3,254,651 | A | 6/1966 | Collito |
| 3,519,187 | A | 7/1970 | Kapitanov et al. |
| 3,774,615 | A | 11/1973 | Lim et al. |
| 4,076,162 | A | 2/1978 | Kapitanov et al. |
| 4,214,587 | A | 7/1980 | Sakura, Jr. |
| 4,241,861 | A | 12/1980 | Fleischer |
| 4,248,267 | A | 2/1981 | Brandenberg |
| 4,318,313 | A | 3/1982 | Tartaglia et al. |
| 4,331,277 | A | 5/1982 | Green |
| 4,350,160 | A | 9/1982 | Kolesov et al. |
| 4,352,358 | A | 10/1982 | Angelchik |
| 4,366,819 | A | 1/1983 | Kaster |
| 4,368,736 | A | 1/1983 | Kaster |
| 4,503,568 | A | 3/1985 | Madras |

(Continued)

FOREIGN PATENT DOCUMENTS

DE 69406845 4/1998

(Continued)

OTHER PUBLICATIONS

Ethicon Endo-Surgery, "Atlas of Surgical Stapling", (1999).

*Primary Examiner* — Tuan Nguyen
*Assistant Examiner* — Thomas McEvoy
(74) *Attorney, Agent, or Firm* — Brian A. Schar (57) ABSTRACT

An exemplary surgical apparatus may include an anvil including an outer surface, a channel defined therein, and an aperture defined in the outer surface, where the aperture opens to the channel; and a cutter slidable along and within the channel, where at least a portion of the cutter is flexible. Another exemplary surgical apparatus may include an anvil including an open channel defined therein; and a one-piece cutter including a knife adjacent to a bending region, where the cutter is slidable in the channel; where the knife is initially held completely within the anvil, and where the knife flexes out of the channel and out of the anvil in response to proximal motion of the cutter. An exemplary surgical method of treating tissue within the body of a patient may include providing a flexible cutter including a knife; providing an anvil with a channel defined therein; holding the knife completely within the channel in a stowed position; placing the anvil adjacent to tissue; and moving the cutter proximally, wherein that moving causes at least part of the knife to flex out of the channel and into the tissue adjacent to the anvil.

10 Claims, 5 Drawing Sheets

U.S. PATENT DOCUMENTS

| | | | |
|---|---|---|---|
| 4,523,592 A | 6/1985 | Daniel | |
| 4,553,542 A | 11/1985 | Schenck et al. | |
| 4,593,693 A | 6/1986 | Schenck | |
| 4,603,693 A | 8/1986 | Conta et al. | |
| 4,605,001 A | 8/1986 | Rothfuss et al. | |
| 4,607,637 A | 8/1986 | Berggren et al. | |
| 4,617,928 A | 10/1986 | Alfranca | |
| 4,624,255 A | 11/1986 | Schenck et al. | |
| 4,624,257 A | 11/1986 | Berggren et al. | |
| 4,633,874 A | 1/1987 | Chow et al. | |
| 4,657,019 A | 4/1987 | Walsh et al. | |
| 4,665,906 A | 5/1987 | Jervis | |
| 4,747,407 A | 5/1988 | Liu et al. | |
| 4,752,024 A | 6/1988 | Green et al. | |
| 4,773,420 A | 9/1988 | Green | |
| 4,907,591 A | 3/1990 | Vasconcellos et al. | |
| 4,917,087 A | 4/1990 | Walsh et al. | |
| 4,917,090 A | 4/1990 | Berggren et al. | |
| 4,917,091 A | 4/1990 | Berggren et al. | |
| 4,930,674 A | 6/1990 | Barak | |
| 4,938,408 A | 7/1990 | Bedi | |
| 4,951,861 A | 8/1990 | Schulze et al. | |
| 5,005,749 A | 4/1991 | Aranyi | |
| 5,018,657 A | 5/1991 | Pedlick et al. | |
| 5,062,842 A | 11/1991 | Tiffany | |
| 5,104,025 A | 4/1992 | Main et al. | |
| 5,119,983 A | 6/1992 | Green et al. | |
| 5,156,310 A | 10/1992 | Biedenharn | |
| 5,156,619 A | 10/1992 | Ehrenfeld | |
| 5,172,845 A | 12/1992 | Tejeiro | |
| 5,178,634 A | 1/1993 | Ramos Martinez | |
| 5,193,731 A | 3/1993 | Aranyi | |
| 5,205,459 A | 4/1993 | Brinkerhoff et al. | |
| 5,211,683 A | 5/1993 | Maginot | |
| 5,234,447 A | 8/1993 | Kaster et al. | |
| 5,250,058 A | 10/1993 | Miller et al. | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,304,220 A | 4/1994 | Maginot | |
| 5,314,435 A | 5/1994 | Green et al. | |
| 5,314,468 A | 5/1994 | Ramos Martinez | |
| 5,333,773 A | 8/1994 | Main et al. | |
| 5,336,233 A | 8/1994 | Chen | |
| 5,350,104 A | 9/1994 | Main et al. | |
| 5,366,462 A | 11/1994 | Kaster et al. | |
| 5,376,095 A | 12/1994 | Ortiz | |
| 5,392,979 A | 2/1995 | Green et al. | |
| 5,395,030 A | 3/1995 | Kuramoto et al. | |
| 5,417,361 A | 5/1995 | Williamson, IV | |
| 5,431,322 A | 7/1995 | Green et al. | |
| 5,443,497 A | 8/1995 | Venbrux | |
| 5,447,514 A | 9/1995 | Gerry et al. | |
| 5,452,836 A | 9/1995 | Huitema et al. | |
| 5,454,825 A | 10/1995 | Van Leeuwen | |
| 5,456,712 A | 10/1995 | Maginot | |
| 5,456,714 A | 10/1995 | Owen | |
| 5,464,449 A | 11/1995 | Ryan et al. | |
| 5,465,895 A | 11/1995 | Knodel et al. | |
| 5,465,896 A | 11/1995 | Allen et al. | |
| 5,478,003 A | 12/1995 | Green et al. | |
| 5,478,354 A | 12/1995 | Tovey et al. | |
| 5,489,058 A | 2/1996 | Plyley et al. | |
| 5,522,834 A | 6/1996 | Fonger et al. | |
| 5,533,661 A | 7/1996 | Main et al. | |
| 5,535,935 A | 7/1996 | Vidal et al. | |
| 5,558,667 A | 9/1996 | Yarborough et al. | |
| 5,562,241 A | 10/1996 | Knodel et al. | |
| 5,571,167 A | 11/1996 | Maginot | |
| 5,580,067 A | 12/1996 | Hamblin et al. | |
| 5,586,711 A | 12/1996 | Plyley et al. | |
| 5,609,285 A | 3/1997 | Grant et al. | |
| 5,620,452 A | 4/1997 | Yoon | |
| 5,632,432 A | 5/1997 | Schulze et al. | |
| 5,632,433 A | 5/1997 | Grant et al. | |
| 5,636,780 A | 6/1997 | Green | |
| 5,643,340 A | 7/1997 | Nunokawa | |
| 5,653,373 A | 8/1997 | Green et al. | |
| 5,655,698 A | 8/1997 | Yoon | |
| 5,657,921 A | 8/1997 | Young et al. | |
| 5,662,258 A | 9/1997 | Knodel et al. | |
| 5,669,544 A | 9/1997 | Schulze et al. | |
| 5,669,918 A | 9/1997 | Balazs et al. | |
| 5,676,670 A | 10/1997 | Kim | |
| 5,693,088 A | 12/1997 | Lazarus | |
| 5,695,504 A | 12/1997 | Gifford, III et al. | |
| 5,702,412 A | 12/1997 | Popov et al. | |
| 5,707,362 A | 1/1998 | Yoon | |
| 5,707,380 A | 1/1998 | Hinchliffe et al. | |
| 5,709,693 A | 1/1998 | Taylor | |
| 5,711,472 A | 1/1998 | Bryan | |
| 5,725,544 A | 3/1998 | Rygaard | |
| 5,797,920 A | 8/1998 | Kim | |
| 5,799,857 A | 9/1998 | Robertson et al. | |
| 5,816,471 A * | 10/1998 | Plyley et al. | 227/178.1 |
| 5,817,113 A | 10/1998 | Gifford, III et al. | |
| 5,833,690 A | 11/1998 | Yates et al. | |
| 5,833,698 A | 11/1998 | Hinchliffe et al. | |
| 5,865,730 A | 2/1999 | Fox et al. | |
| 5,878,938 A | 3/1999 | Bittner et al. | |
| 5,879,371 A | 3/1999 | Gardiner et al. | |
| 5,915,616 A | 6/1999 | Viola et al. | |
| 5,918,791 A | 7/1999 | Sorrentino et al. | |
| 5,921,995 A | 7/1999 | Kleshinski | |
| 5,944,730 A | 8/1999 | Nobles et al. | |
| 5,976,159 A | 11/1999 | Bolduc | |
| 5,993,464 A | 11/1999 | Knodel | |
| 6,015,416 A | 1/2000 | Stefanchik et al. | |
| 6,024,748 A | 2/2000 | Manzo et al. | |
| 6,036,700 A | 3/2000 | Stefanchik et al. | |
| 6,039,733 A | 3/2000 | Buysse et al. | |
| 6,050,472 A | 4/2000 | Shibata | |
| 6,053,390 A | 4/2000 | Green et al. | |
| 6,066,144 A | 5/2000 | Wolf et al. | |
| 6,066,148 A | 5/2000 | Rygaard | |
| 6,071,289 A | 6/2000 | Stefanchik et al. | |
| 6,083,234 A | 7/2000 | Nicholas et al. | |
| 6,110,187 A | 8/2000 | Donlon | |
| 6,117,148 A | 9/2000 | Ravo et al. | |
| 6,176,413 B1 | 1/2001 | Heck et al. | |
| 6,183,486 B1 | 2/2001 | Snow et al. | |
| 6,187,019 B1 | 2/2001 | Stefanchik | |
| 6,193,129 B1 | 2/2001 | Bittner et al. | |
| 6,193,734 B1 | 2/2001 | Bolduc et al. | |
| 6,200,263 B1 | 3/2001 | Person | |
| 6,209,773 B1 | 4/2001 | Bolduc et al. | |
| 6,248,117 B1 | 6/2001 | Blatter | |
| 6,254,617 B1 | 7/2001 | Spence et al. | |
| 6,280,460 B1 | 8/2001 | Bolduc et al. | |
| 6,394,948 B1 | 5/2002 | Borst et al. | |
| 6,436,097 B1 | 8/2002 | Nardella | |
| 6,461,365 B2 | 10/2002 | Bolduc et al. | |
| 6,514,263 B1 | 2/2003 | Stefanchik et al. | |
| 6,520,973 B1 | 2/2003 | McGarry | |
| 6,530,932 B1 | 3/2003 | Swayze | |
| 6,551,334 B2 | 4/2003 | Blatter et al. | |
| 6,569,173 B1 | 5/2003 | Blatter et al. | |
| 6,623,494 B1 | 9/2003 | Blatter | |
| 6,626,921 B2 | 9/2003 | Blatter et al. | |
| 6,652,542 B2 | 11/2003 | Blatter et al. | |
| 6,663,590 B2 | 12/2003 | Blatter | |
| 6,726,694 B2 | 4/2004 | Blatter et al. | |
| 6,736,825 B2 | 5/2004 | Blatter et al. | |
| 6,743,244 B2 | 6/2004 | Blatter et al. | |
| 6,821,286 B1 | 11/2004 | Carranza et al. | |
| 6,905,504 B1 | 6/2005 | Vargas | |
| 6,942,675 B1 | 9/2005 | Vargas | |
| 7,285,131 B1 * | 10/2007 | Bombard et al. | 623/1.36 |
| 2001/0004698 A1 | 6/2001 | Blatter et al. | |
| 2001/0023353 A1 | 9/2001 | Vargas et al. | |
| 2001/0023354 A1 | 9/2001 | Blatter et al. | |
| 2002/0095166 A1 | 7/2002 | Vargas et al. | |
| 2003/0014064 A1 | 1/2003 | Blatter | |
| 2004/0097994 A1 | 5/2004 | Blatter et al. | |
| 2004/0199181 A1 * | 10/2004 | Knodel et al. | 606/139 |
| 2004/0225306 A1 | 11/2004 | Blatter et al. | |

| | | | |
|---|---|---|---|
| 2005/0216043 A1 | 9/2005 | Blatter et al. | |
| 2005/0267496 A1 | 12/2005 | Loshakove et al. | |
| 2006/0167485 A1 | 7/2006 | Blatter | |

FOREIGN PATENT DOCUMENTS

| | | |
|---|---|---|
| DE | 19732234 | 1/1999 |
| EP | 1354559 A2 | 5/1995 |
| EP | 0625335 B1 | 11/1997 |
| EP | 0820724 | 1/1998 |
| EP | 0885595 | 12/1998 |
| EP | 0938870 | 9/1999 |
| EP | 0820725 | 1/2000 |
| EP | 0990420 | 4/2000 |
| FR | 2316910 | 7/1976 |
| SU | 1667844 | 8/1991 |
| WO | WO-98/19625 | 5/1998 |
| WO | WO-99/11178 | 3/1999 |
| WO | WO-99/21491 | 5/1999 |
| WO | WO-00/12013 | 3/2000 |
| WO | WO-00/59380 | 10/2000 |

* cited by examiner

FLEXIBLE CUTTER FOR SURGICAL STAPLER

FIELD OF THE INVENTION

The invention generally relates to surgical staplers, and more specifically to cutters utilized in surgical staplers to cut tissue.

BACKGROUND

Surgical staplers, such as utilized in anastomosis procedures, transection of tissue, and other procedures, generally include one or more staples and an anvil against which those staples are deformed. Surgical staplers often additionally include a knife that is used to cut tissue after, during or before staples are deployed adjacent to that tissue. For example, U.S. Pat. No. 7,285,131 and U.S. patent application Ser. No. 11/935,315 filed on Nov. 5, 2007, both of which are hereby incorporated by reference in their entirety (the "Anvil Documents") describe an anvil sized for placement in a target blood vessel, where staples are deployed from outside the coronary artery against the anvil to connect a graft vessel to the target vessel. The anvils disclosed in the Anvil Documents each include a knife, and a channel along which the knife can slide. The knife is initially in a first position stowed inside the anvil, then moves to a position above the anvil in order to cut the wall of the target vessel and allow blood to flow between the graft vessel and the target vessel, thereby completing the anastomosis. The knife is then moved back to a second position stowed within the anvil, different from the first position. The Anvil Documents describe single-user tools that cannot be refired. One reason is that the first and second stowed positions of the knife within the anvil are different.

BRIEF DESCRIPTION OF THE DRAWINGS

The use of the same reference symbols in different figures indicates similar or identical items.

DETAILED DESCRIPTION

Figure 1:
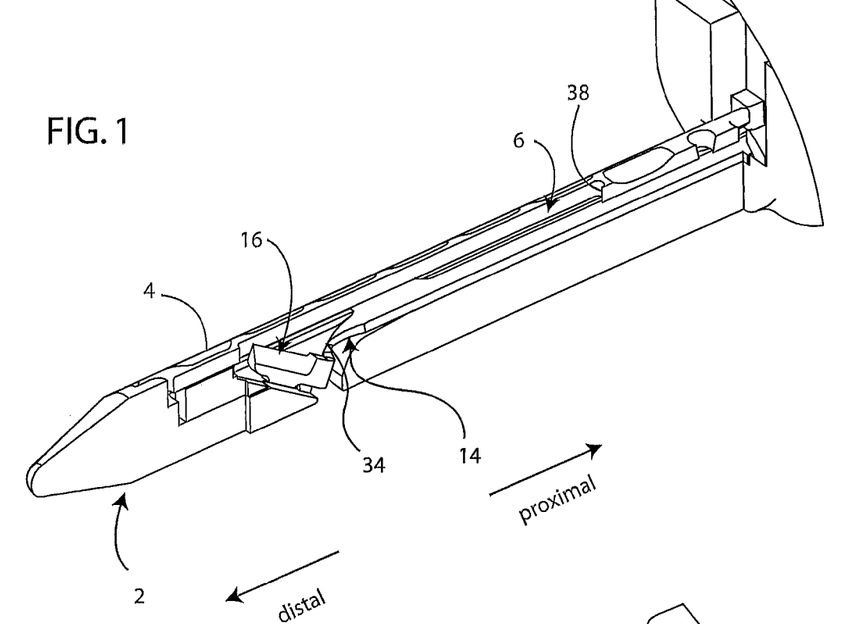
FIG. 1 is a cutaway perspective view of an exemplary anvil in which an exemplary cutter is located in a first position.

Referring to FIG. 1, a surgical stapler includes an anvil 2. Staples may be driven against the anvil 2 by any suitable staple holder, such as described in the Anvil Documents; the particular stapling mechanism utilized is not important to the invention. The anvil 2 may be generally elongated in the longitudinal direction, or may be shaped in any other suitable manner. The anvil 2 includes an upper surface 4, and a longitudinally-extending aperture 6 defined through the upper surface 4. The aperture 6 opens to a channel 8 as seen most clearly in FIG. 3. The channel 8 may include a proximal section 10 and a distal section 12 open to one another. The proximal section 10 may be smaller in cross-sectional area than the distal section 12, and may have a generally-rectangular cross-section along a plane perpendicular to the longitudinal centerline of the anvil 2. Alternately, the proximal section 10 may be shaped in any other suitable manner. The distal section 12 may be roughly triangular in shape, as viewed from the side, or may be shaped in any other suitable manner. The distal section 12 is shaped and sized to hold a knife in a stowed position.

Figure 5:
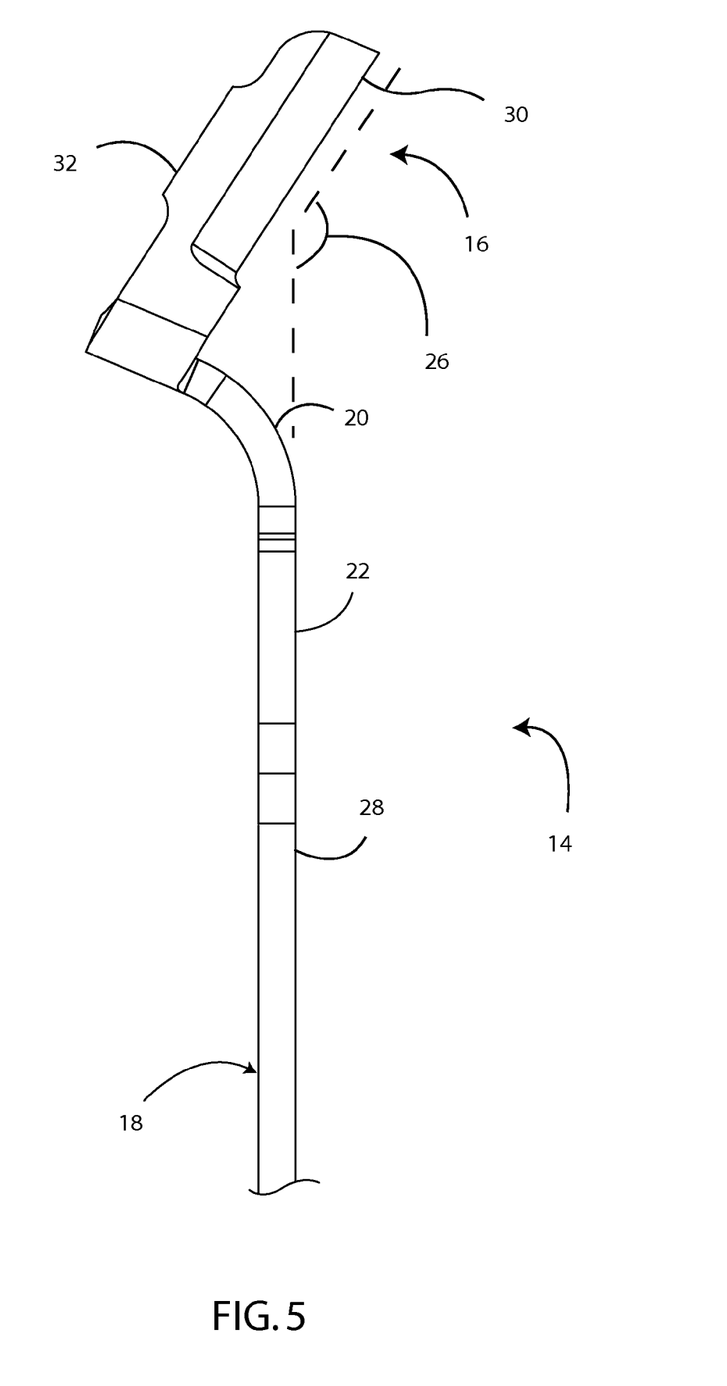
FIG. 5 is a side view of the cutter of FIG. 1.
Figure 6:
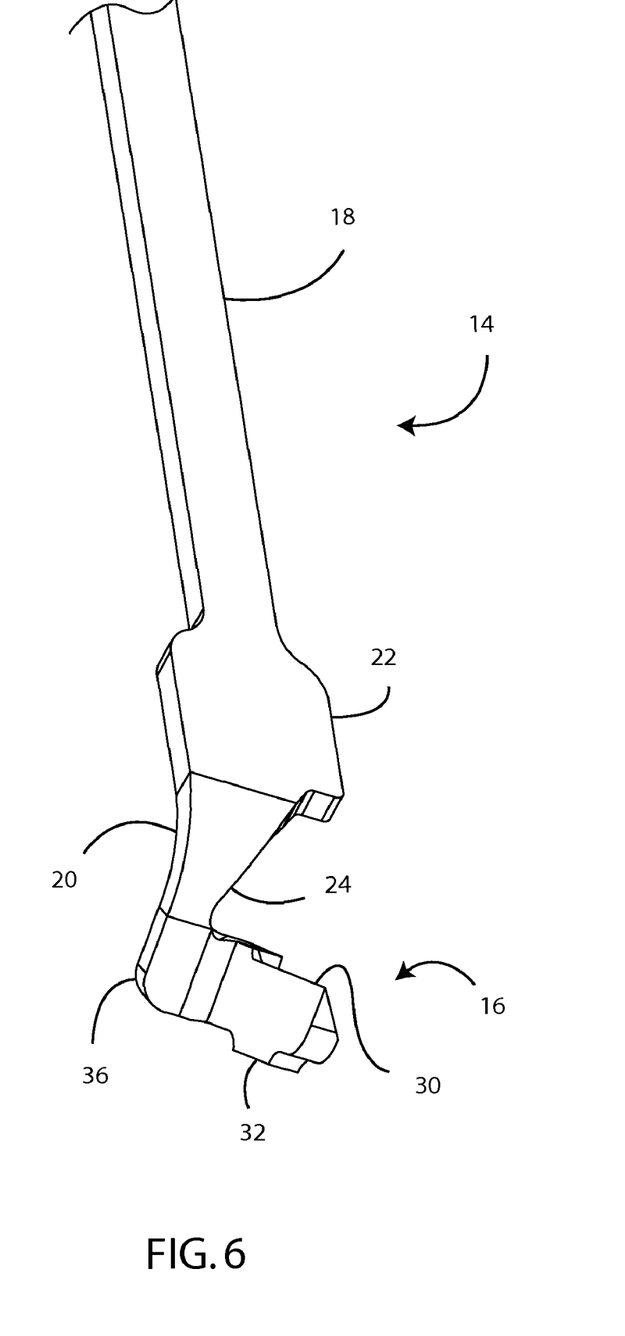
FIG. 6 is a perspective view of the cutter of FIG. 1.

Referring also to FIGS. 5-6, a cutter 14 is configured to slide along the channel 8. The cutter 14 may include a knife 16 at the distal end of an arm 18. The arm 18 may be generally linear along part or most of its length, and may have a rectangular cross-section or other suitable cross-section. The proximal section 10 of the channel 8 may have a cross-section shaped the same as the cross-section of the arm 18. The proximal section 10 of the channel 8 also may be slightly larger in size than the cross-section of the arm 18, in order to allow the arm 18 to slide within the proximal section 10 of the channel 8 while at the same time constraining motion of the arm 18 in directions other than longitudinally. The proximal end of the arm 18 may be connected to a cable, rod or other structure or mechanism that is used to move the cutter 14 along the channel 8. Such a connection may be accomplished, for example, as set forth in the Anvil Documents. The distal end of the arm 18 may be curved or bent downward, resulting in a curved region 20 at the distal end of the arm. The arm 18 may include a wide area 22 immediately proximal to the curved region 20, where the wide area 22 is wider laterally than the portion of the arm 18 proximal to the wide area 22. Alternately, the wide area 22 may be wider in a different direction, or may be omitted. The curved region 20 may taper downward in width in the distal direction along part or all of its length. As a result, the cross-sectional area of the curved region 20 may decrease moving distally along the curved region. The tapered area of the curved region 20 may be referred to as the bending region 24. The knife 16 may extend from the distal end of the curved region 20. The knife 16 may be generally perpendicular to the part of the curved region 20 from which it extends, or may be angled differently relative to the curved region 20. The knife 16 may extend from a lateral edge of the curved region 20. If so, the portion of the curved region 20 laterally adjacent to the knife 16 may be referred to as the ledge 36. Further, the knife 16 may form an obtuse angle 26 with the upper surface of the arm 18. The knife 16 includes a cutting edge 30 that is oriented generally upward. The opposite side 32 of the knife 16 may be blunt. The shape of the cutter 14 described here and shown in FIGS. 5-6 is the shape assumed by the cutter 14 in a neutral state. The "neutral state" means the state in which no external forces are acting upon the cutter 14. Alternately, the shape of the cutter 14 shown in FIGS. 5-6 may be the deformed shape of the cutter 14 that the cutter 14 assumes when forced into an initial position.

The cutter 14 may be fabricated as a single piece, such as by stamping, molding, laser cutting, machining, or any other suitable process or combination of processes. Alternately, the knife 16 may be fabricated separately from the arm 18 and attached to the arm 18 by any suitable method or structure, such as by welding. The cutter 14 may be fabricated from any suitable material. Advantageously, the cutter 14 is fabricated from a superelastic alloy such as nitinol. As another example, the cutter 14 may be fabricated from an elastically deformable material. Such material may be, for example, an amorphous zirconium-based metal alloy such as Vitreloy. As another example, the cutter 14 may be composed of a plastically-deformable material, where bending in the bending region 24 causes stress in the cutter 14 that is less than the yield point of the material from which the cutter 14 is fabricated.

Referring also to FIG. 1, the cutter 14 is in its initial position within the anvil 2 such that the majority of the arm 18 is located in the proximal section 10 of the channel 8, and the knife 16 and the curved region 20 of the arm 18 are located in the distal section 12 of the channel 8. In the initial position of the cutter 14 within the channel 8, the knife 16 is located entirely within the channel 8. When the cutter 14 is in the initial position, the knife 16 may be referred to as being in the initial position or as being in the stowed position. The knife 16 does not extend out of the aperture 6 in the upper surface 4 of the anvil 2 in the initial position of the cutter 14. In this way, the anvil 2 can be inserted into tissue without the risk of the knife 16 cutting that tissue. The anvil 2 may include a cam surface 34 defined in the distal section 12 of the channel 8. The cam surface 34 may be curved downward proximally to distally, or may be shaped in any other suitable manner. When the cutter 14 is in the initial position completely within the channel 8 in the anvil 2, the cam surface 34 engages the ledge 36 of the curved surface 20 of the cutter 14, and/or a remainder of the curved surface 20. This contact between the cam surface 34 and the ledge 36 and/or a remainder of the curved surface 20 may push the knife 16 downward relative to its neutral state, such that the obtuse angle 26 between the arm 18 and the knife 16 is greater than in the neutral state. Alternately, the cam surface 34 and the cutter 14 are configured such that the cutter 14 is in the neutral state when in the initial position in the channel 8 in the anvil 2.

Operation

Placement of the anvil 2 relative to tissue, and actuation of the cutter 14, may be substantially as described in the Anvil Documents. For clarity and brevity, the differences between that operation described in the Anvil Documents and the operation of the cutter 14 of this document are described here. The anvil 2 is placed in proximity to tissue to be treated, such as inside the lumen of a target vessel. The cutter 14 is then actuated, such as by depressing a firing trigger on a handle.

Figure 2:
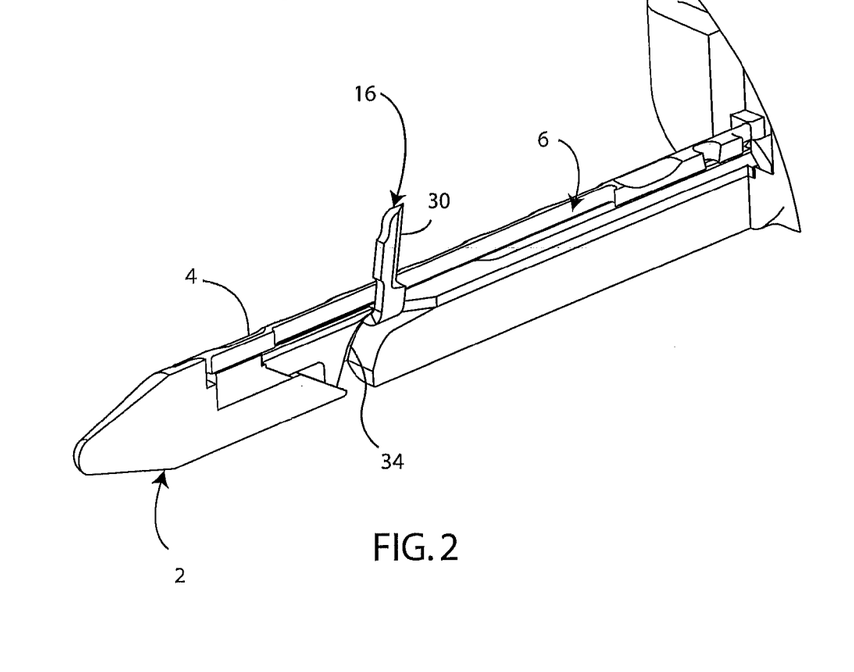
FIG. 2 is a cutaway perspective view of the anvil of FIG. 1, in which the cutter is located in a second position.

Referring also to FIG. 1, upon actuation of the cutter 14, the arm 18 is pulled proximally. The knife 16 moves proximally as well. The ledge 36 adjacent to the knife 16 slides proximally, along the cam surface 34. As the knife 16 moves proximally, it also moves upward, as the curved region 20 of the arm 18 relaxes into its neutral state. As the knife 16 moves upward, the cutting edge 30 of the knife 16 moves upward through and out of the aperture 6 in the channel 8. That is, the knife 16 flexes upward through and out of the aperture 6, as the force previously holding the knife 16 down in the stowed position is gradually removed. As the cutting edge 30 moves out of the aperture 6, it penetrates tissue adjacent to the upper surface 4 of the anvil 2. As the ledge 36 moves proximally and upward along the cam surface 34, the curved region 20 of the arm 18 may relax into its neutral state, such that the obtuse angle 26 between the knife 16 and the upper surface of the arm 28 decreases. As the ledge 36 then continues to move proximally and upward along the cam surface 34, the curved region 20 of the arm 18 enters the proximal section 10 of the channel 8. The entry of the curved region 20 into the generally-rectangular proximal section 10 of the channel 8 causes the curved region 20 to bend into a straighter shape, causing the obtuse angle 26 between the knife 16 and the upper surface 28 of the arm 18 to decrease further. Referring also to FIG. 2, when the curved region 20 of the arm 18 has completely entered the proximal section 10 of the channel 8, the knife 16 has moved upward out of the aperture 6 to its maximum extent, which may be referred to as the cutting configuration of the knife 16. In the cutting configuration, the obtuse angle 26 between the knife 16 and the upper surface of the arm 28 may be substantially a right angle, or slightly greater than a right angle. Alternately, the obtuse angle 26 may become an acute angle in the cutting configuration.

Figure 3:
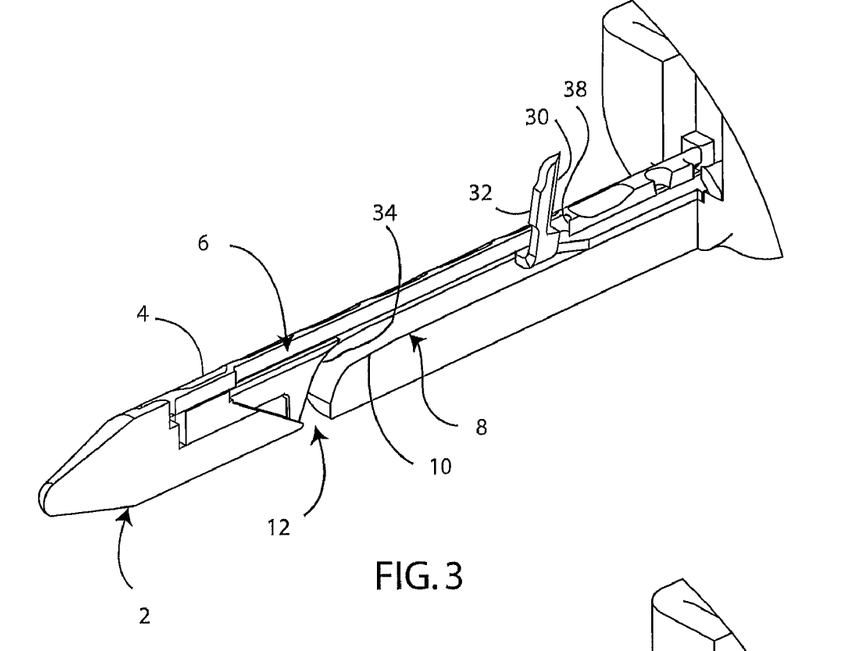
FIG. 3 is a cutaway perspective view of the anvil of FIG. 1, in which the cutter is located in a third position.

The arm 18 continues to be pulled proximally. As a result, the knife 16 moves proximally. The cutting edge 30 faces proximally, such that proximal motion of the knife 16 creates an incision in the tissue previously penetrated by the knife 16 when the knife 16 moved up and out of the aperture 6 in the upper surface 4 of the anvil 2. The arm 18 continues to move proximally until it stops. Proximal motion of the arm 18 may stop due to an encounter between the knife 16 and the proximal end 38 of the aperture 6, due to cessation of actuation of the cutter 14 in the proximal direction, or a combination of both. Referring also to FIG. 3, the knife 16 is then in the most-proximal location, and the incision of tissue adjacent to the upper surface 4 of the anvil 2 is complete. Before, during and/or after motion of the knife 16 to the most-proximal location, staples may be deployed into the tissue adjacent to the upper surface 4 of the anvil 2 as set forth in the Anvil Documents, or that tissue may be otherwise treated.

Figure 4:
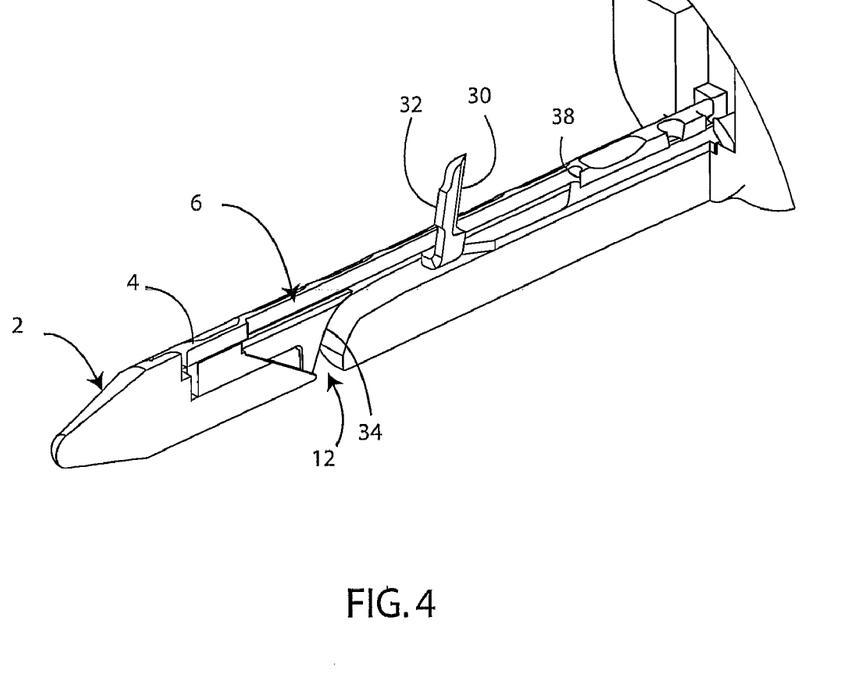
FIG. 4 is a cutaway perspective view of the anvil of FIG. 1, in which the cutter is located in a fourth position.

The cutter 14 is then actuated to move distally. Referring also to FIG. 4, the knife 16 consequently moves distally from its previous, most-proximal location. As the knife 16 moves distally, its blunt side 32 leads, such that the blunt side 32 of the knife 16 does not further incise tissue during distal travel of the knife 16. As the knife 16 continues to move distally, the ledge 36 at the distal end of the curved region 20 of the arm 18 slides under the proximal end of the cam surface 34. As the cutter 14 continues to move distally, the curved region 20 of the arm 18 begins to move out of the proximal section 10 of the channel 8, allowing the cutter 14 to return toward its neutral state. Further, engagement between the cam surface 34 and the ledge 36 urges the cutter 14 to move back toward its neutral state. As the cutter 14 returns toward its neutral state, the obtuse angle 26 between the knife 16 and the upper surface 28 of the arm 18 increases. After the cutter 14 returns to its neutral state, the cutter 14 may still continue to be urged distally if the knife 16 has not reached its initial position. Contact between the ledge 36 and the cam surface 34 causes the curved region 20 to bend such that the obtuse angle 26 between the knife 16 and the upper surface 28 of the arm 18 increases further. The cutter 14 moves distally until the knife 16 reaches its initial position, completely within the channel 8 in the anvil 2. The anvil 2 can then be removed from tissue, or reused within the same tissue. By returning the cutter 14 to its initial position after it has incised tissue, the cutter 14 can be actuated multiple times from that initial position.

Reverse Knife

Figure 7:
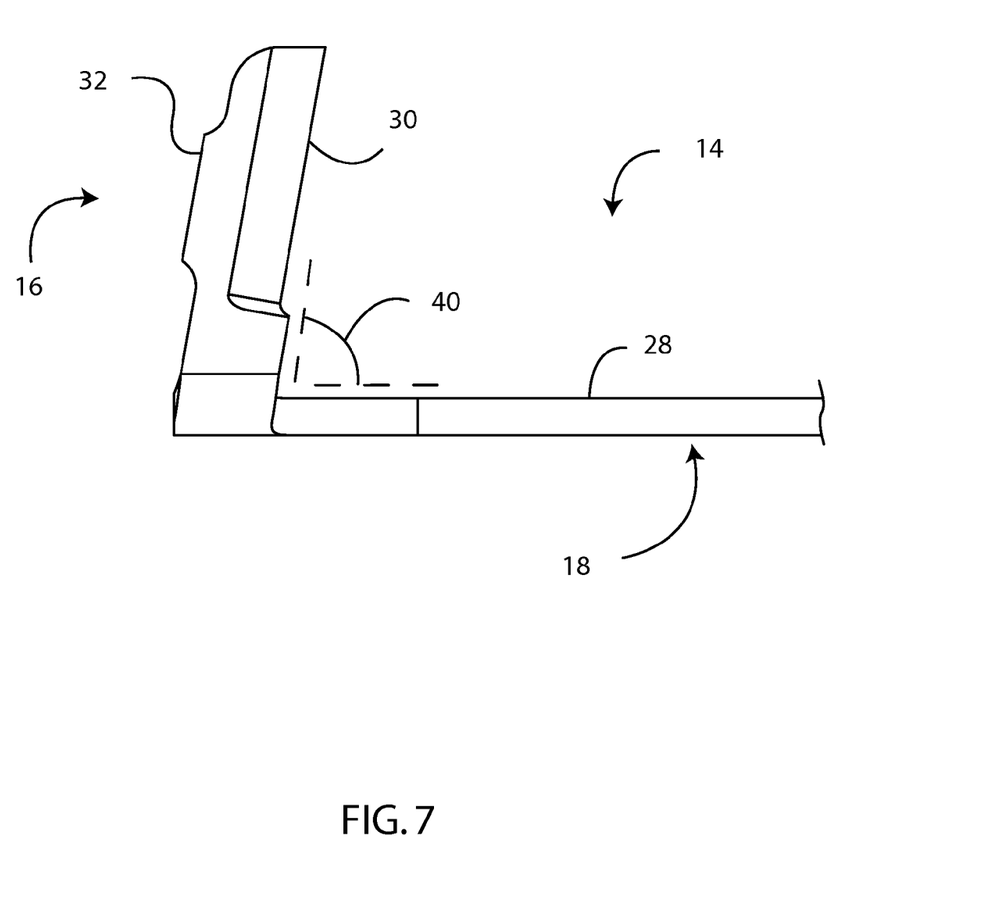
FIG. 7 is a side view of another exemplary cutter.

Referring to FIG. 7, another exemplary embodiment of the cutter 14 is shown. In this embodiment, the knife 16 forms an acute angle 40 with the upper surface 28 of the arm 18 in the neutral state. The cutting edge 30 extends onto the top of the knife 16. Further, the curved region 20 is not present in this embodiment; however, the bending region 24 is present, and the arm 18 is tapered in the bending region. In other respects, the cutter 14 is as set forth above. The anvil 2 is also substantially as set forth above, with the exception that the cam surface 34 can be eliminated.

Operation of this embodiment of the cutter 14 is substantially as described above. For clarity and brevity, the differences between that operation and the operation of the cutter 14 of FIG. 7 are described here. The distal portion 12 of the channel 8 extends distal to the distal end of the aperture 6, and the knife 16 is located in that distal portion 12 of the channel 8 in the initial position of the cutter 14. The distal portion 12 of the channel 8 compresses the knife 16 down. As the cutter 14 is pulled proximally, the knife 16 is free to move upward to its neutral position. As the knife 16 moves upward, the cutting edge 30 on the upper surface of the knife 16 penetrates tissue adjacent to the upper surface 4 of the anvil 2. As described above, as the cutter 14 is moved proximally, the cutting edge 30 of the knife 16 incises tissue adjacent to the upper surface of the anvil 2. The cutter 14 is then moved distally. As the blunt side 32 of the knife 16 encounters the distal end of the aperture 6, that contact pushes the knife 16 downward, and the knife 16 moves downward and slides into the distal portion 12 of the channel 18 distal to the aperture 6. The knife 16 has thus returned to its initial, stowed position.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus suitable for cutting tissue, comprising:
    an anvil including an outer surface, a channel defined therein, and an aperture defined in said outer surface, said aperture opening to said channel; and
    a cutter slidable along and within said channel, said cutter comprising an arm with a substantially rectangular cross section that is wider than it is tall and that includes a downwardly-curved arcuate region at the distal end thereof, and a knife extending from the distal end of said arcuate region; wherein said arcuate region is flexible; said knife further including a cutting edge oriented upward toward said aperture; wherein said knife forms an obtuse angle with an upper surface of said arm when said cutter is in a neutral state;
    wherein said arm is movable longitudinally from a first position in which said knife is oriented at a non-perpendicular angle to said arm and in which said cutter is located substantially completely within said channel in said anvil to a second position in which said knife is substantially perpendicular to said arm, and wherein said arcuate region bends upward as said arm moves from said first position to said second position to cause at least a portion of said knife to move out of said anvil through said aperture in said outer surface.

2. The surgical apparatus of claim 1, incorporating by reference all of the elements of that claim; wherein said cutter is superelastic.

3. The surgical apparatus of claim 1, incorporating by reference all of the elements of that claim; wherein said arcuate region is tapered downward in width toward the distal direction.

4. The surgical apparatus of claim 1, incorporating by reference all of the elements of that claim; wherein said knife extends from a lateral edge of said arcuate region.

5. The surgical apparatus of claim 1, incorporating by reference all of the elements of that claim; wherein said knife includes a cutting edge on one side oriented generally upward, and a blunt side on the opposite side from said cutting edge.

6. The surgical apparatus of claim 1, incorporating by reference all of the elements of that claim; wherein said channel includes a proximal section and a distal section, wherein said proximal section has a cross-section shaped substantially the same as the cross-section of the arm, and wherein said proximal section of said channel constrains motion of said arm in directions other than substantially longitudinal.

7. The surgical apparatus of claim 1, incorporating by reference all of the elements of that claim; wherein said cutter is movable proximally, and wherein said knife flexes from said first position out through said aperture in response to proximal motion of said cutter.

8. The surgical apparatus of claim 1, incorporating by reference all of the elements of that claim; wherein said knife is initially held completely within the anvil in a stowed position.

9. The surgical apparatus of claim 8, incorporating by reference all of the elements of that claim; wherein said arm further comprises a ledge adjacent said knife, and wherein said anvil further comprises a cam surface defined in said channel curved downward proximally to distally; wherein said ledge engages said cam surface when said knife is in said stowed position.

10. The surgical apparatus of claim 9, incorporating by reference all of the elements of that claim; wherein said cam surface exerts a downward force on said ledge when said knife is in said stowed position.

* * * * *